(12) United States Patent
Hipp et al.

(10) Patent No.: US 11,994,664 B2
(45) Date of Patent: May 28, 2024

(54) AUGMENTED REALITY LASER CAPTURE MICRODISSECTION MACHINE

(71) Applicant: GOOGLE LLC, Mountain View, CA (US)

(72) Inventors: Jason Hipp, Mountain View, CA (US); Martin Stumpe, Mountain View, CA (US)

(73) Assignee: Google LLC, Mountain View, CA (US)

(*) Notice: Subject to any disclaimer, the term of this patent is extended or adjusted under 35 U.S.C. 154(b) by 460 days.

(21) Appl. No.: 17/295,353

(22) PCT Filed: Oct. 31, 2019

(86) PCT No.: PCT/US2019/059215
§ 371 (c)(1),
(2) Date: May 19, 2021

(87) PCT Pub. No.: WO2020/146037
PCT Pub. Date: Jul. 16, 2020

(65) Prior Publication Data
US 2022/0019069 A1 Jan. 20, 2022

Related U.S. Application Data

(60) Provisional application No. 62/790,221, filed on Jan. 9, 2019.

(51) Int. Cl.
*G02B 21/32* (2006.01)
*G02B 21/36* (2006.01)
(Continued)

(52) U.S. Cl.
CPC .......... *G02B 21/32* (2013.01); *G02B 21/365* (2013.01); *G06F 3/167* (2013.01); *G06N 20/00* (2019.01)

(58) Field of Classification Search
CPC ...... G02B 21/32; G02B 21/365; G02B 21/00; G02B 21/0004; G02B 21/0012;
(Continued)

(56) References Cited

U.S. PATENT DOCUMENTS 5,998,129 A 12/1999 Schutze et al.
7,915,016 B2 3/2011 Liss
(Continued)

FOREIGN PATENT DOCUMENTS

WO 2009086521 A1 7/2009
WO 2016130424 A1 8/2016
(Continued)

OTHER PUBLICATIONS

PCT International Search Report and Written Opinion, Application No. PCT/US2019/059215, mailed Jan. 29, 2020, 12 pages.
(Continued)

*Primary Examiner* — Arnel C Lavarias
(74) *Attorney, Agent, or Firm* — McDonnell Boehnen Hulbert & Berghoff LLP

(57) ABSTRACT

An augmented reality (AR) subsystem including one or more machine learning models, automatically overlays an augmented reality image, e.g., a border or outline, that identifies cells of potential interest, in the field of view of the specimen as seen through the eyepiece of an LCM microscope. The operator does not have to manually identify the cells of interest for subsequent LCM, e.g, on a workstation monitor, as in the prior art. The operator is provided with a switch, operator interface tool or other mechanism to select the identification of the cells, that is, indicate approval of the identification of the cells, while they view the specimen through the eyepiece. Activation of the switch or other mechanism invokes laser excising and capture of the cells of interest via a known and conventional LCM subsystem.

15 Claims, 3 Drawing Sheets

(51) Int. Cl.
  *G06F 3/16* (2006.01)
  *G06N 20/00* (2019.01)
(58) Field of Classification Search
  CPC ............ G02B 21/002; G02B 21/00525; G02B 21/006; G02B 21/008; G02B 21/18; G02B 21/24; G02B 21/36; G02B 21/367; G06F 3/167; G06N 20/00; G06N 5/00; G06N 5/04
  USPC .... 359/368, 362, 363, 369, 372; 706/12, 45, 706/46, 47
  See application file for complete search history.

(56) References Cited

U.S. PATENT DOCUMENTS

| | | | |
|---|---|---|---|
| 8,664,002 B2 | 3/2014 | Yeung | |
| 9,103,757 B2 | 8/2015 | Baer et al. | |
| 9,279,749 B2 | 3/2016 | Donovan et al. | |
| 9,664,599 B2 | 5/2017 | Gogler | |
| 9,804,144 B2 | 10/2017 | Schlaudraff et al. | |
| 2015/0262329 A1 | 9/2015 | Vink et al. | |
| 2016/0018779 A1 | 1/2016 | Takano | |
| 2016/0063359 A1 | 3/2016 | Szegedy et al. | |
| 2017/0243085 A1 | 8/2017 | Vanhoucke et al. | |
| 2018/0114317 A1 | 4/2018 | Song et al. | |
| 2018/0149561 A1 | 5/2018 | Schlaudraff et al. | |
| 2020/0097727 A1* | 3/2020 | Stumpe | G02B 21/361 |
| 2021/0018742 A1* | 1/2021 | Stumpe | G06T 7/62 |

FOREIGN PATENT DOCUMENTS

| | | |
|---|---|---|
| WO | 2018156133 A1 | 8/2018 |
| WO | 2018231204 A1 | 12/2018 |
| WO | 2019199392 A1 | 10/2019 |

OTHER PUBLICATIONS

Paduano, Vincenzo, Maria Teresa De Angelis, Geppino Falco, and Michele Ceccarelli. "Fully automated organ bud detection and segmentation for Laser Capture Microdissection applications." In 2011 IEEE International Conference on Imaging Systems and Techniques, pp. 118-123. IEEE, 2011.

Watson, Jeffrey R., Christian F. Gainer, Nikolay Martirosyan, Jesse Skoch, G. Michael Lemole Jr, Rein Anton, and Marek Romanowski. "Augmented microscopy: real-time overlay of bright-field and near-infrared fluorescence images." Journal of biomedical optics 20, No. 10 (2015): 106002.

Edwards, P. J., D. J. Hawkes, D. L. G. Hill, D. Jewell, R. Spink, A. Strong, and M. Gleeson. "Augmentation of reality using an operating microscope for otolaryngology and neurosurgical guidance." Journal of image guided surgery 1, No. 3 (1995): 172-178.

Philip, J., Andrew P. King, David J. Hawkes, Oliver Fleig, Calvin R. Maurer Jr, Derek LG Hill, Michael R. Fenlon et al. "Stereo Augmented Reality in the Surgical Microscope." In Medicine Meets Virtual Reality, pp. 102-108. IOS Press, 1999.

Brasko, Csilla, Kevin Smith, Csaba Molnar, Nora Farago, Lili Hegedus, Arpad Balind, Tamas Balassa et al. "Intelligent image-based in situ single-cell isolation." Nature communications 9, No. 1 (2018): 1-7.

Szegedy, Christian, Wei Liu, Yangqing Jia, Pierre Sermanet, Scott Reed, Dragomir Anguelov, Dumitru Erhan, Vincent Vanhoucke, and Andrew Rabinovich. "Going deeper with convolutions." In Proceedings of the IEEE conference on computer vision and pattern recognition, pp. 1-9. 2015.

Szegedy, Christian, Vincent Vanhoucke, Sergey Ioffe, Jon Shlens, and Zbigniew Wojna. "Rethinking the inception architecture for computer vision." In Proceedings of the IEEE conference on computer vision and pattern recognition, pp. 2818-2826. 2016.

Szegedy, Christian, Sergey Ioffe, Vincent Vanhoucke, and Alexander Alemi. "Inception-v4, inception-resnet and the impact of residual connections on learning." In Proceedings of the AAAI Conference on Artificial Intelligence, vol. 31, No. 1. 2017.

Itjens, Geert, Clara I. Sánchez, Nadya Timofeeva, Meyke Hermsen, Iris Nagtegaal, Iringo Kovacs, Christina Hulsbergen-Van De Kaa, Peter Bult, Bram Van Ginneken, and Jeroen Van Der Laak. "Deep learning as a tool for increased accuracy and efficiency of histopathological diagnosis." Scientific reports 6, No. 1 (2016): 1-11.

Wang, Dayong, Aditya Khosla, Rishab Gargeya, Humayun Irshad, and Andrew H. Beck. "Deep learning for identifying metastatic breast cancer." arXiv preprint arXiv:1606.05718 (2016).

Madabhushi, Anant, and George Lee. "Image analysis and machine learning in digital pathology: Challenges and opportunities." Medical image analysis 33 (2016): 170-175.

Schaumberg, Andrew J., Mark A. Rubin, and Thomas J. Fuchs. "H&E-stained whole slide image deep learning predicts SPOP mutation state in prostate cancer." BioRxiv (2018): 064279.

PCT International Preliminary Report on Patentability, Application No. PCT/US2019/059215, mailed Jun. 16, 2021, 8 pages.

\* cited by examiner

AUGMENTED REALITY LASER CAPTURE MICRODISSECTION MACHINE

CROSS-REFERENCE TO RELATED APPLICATIONS

The present application is a national stage entry of PCT/US2019/059215 filed on Oct. 31, 2019, which claims priority to U.S. provisional application No. 62/790,221 filed on Jan. 9, 2019, the contents of each of which are hereby incorporated by reference.

This disclosure is directed to a laser capture microdissection (LCM) machine which includes an augmented reality (AR) viewing feature and automated identification of potential cells of interest for excision and capture by the LCM machine.

BACKGROUND

Laser capture microdissection is a technique for isolating and extracting specific groups of cells of interest from microscopic regions in tissue samples. Special purpose LCM machines are currently commercially available from several different manufacturers and described in the patent and scientific literature. Such machines typically include a microscope for allowing the operator to view the specimen under magnification. After an operator has designated specific groups of cells of interest, typically on a workstation monitor, lasers are guided to the corresponding location in the microscope slide to excise the area of interest from the slide. A capture mechanism captures the groups of cells and places them in a suitable medium or on a substrate.

The Assigned of this disclosure has described an augmented reality microscope in PCT application PCT/US2017/037212, published as WO 2018/231204 on Dec. 20, 2018, the content of which is incorporated by reference herein.

SUMMARY

In a first aspect, an augmented reality laser capture microdissection machine is disclosed. The machine is configured for capturing cells of interest from a sample. The machine includes: a) a microscope having an eyepiece and a camera configured to capture images of the field of view of the microscope as seen through the eyepiece; b) an augmented reality subsystem configured to receive the images from the camera, the subsystem including a machine learning model stored on a machine readable medium identifying cells of potential interest in the images and a optics module projecting into the view of the microscope as seen through the eyepiece an outline of cells of potential interest identified by the machine learning model; c) a laser capture and microdissection subsystem configured for excising the cells of interest from the sample with one or more lasers and placing such cells of interest on a suitable medium; and d) an operator-activated input mechanism configured to provide input to the laser capture and microdissection subsystem whereby operator activation of the input mechanism while viewing the specimen and the outline of cells identified by the machine learning model at the eyepiece invokes the laser capture and microdissection subsystem so as to excise the cells of interest from the sample within the outline and place them on the medium.

In one configuration, the input mechanism is activated while the operator is viewing the specimen and the outline of cells identified by the machine learning model at the eyepiece, e.g., by activating a voice command, activating a foot switch, clicking a mouse, or taking some other specified action.

In another aspect, a method is described for capturing cells of interest from a sample with the aid of a microscope having an eyepiece. The method includes the steps of a) projecting an augmented reality image into the field of view of the microscope as seen through the eyepiece, the augmented reality image identifying cells of potential interest for laser capture microdissection, typically in the form of a border or outline; and b) invoking a laser capture and microdissection subsystem coupled to the microscope so as to excise the cells of potential interest, as presented in the augmented reality image, from the sample in response to an operator instruction and place them on a suitable medium.

In one configuration, method includes repeating steps a) and b) as an operator of the microscope changes magnification or navigates to different areas of the sample with the microscope.

In one embodiment, in step b) the operator instruction is received while the operator is viewing the specimen through the eyepiece of the microscope. In other words, the operator does not have to look away from the specimen and perform a manual annotation task on an external device to draw a circle or specify a cluster of cells of interest; rather the augmented reality outline of the cells of interest are presented to the operator while they view the specimen through the eyepiece and they invoke the LCM subsystem to capture the cells of interest within the outline by a simple command, such as voice activated switch, foot switch, clicking a mouse, or other direct operation.

In another aspect, an improvement to a machine including a microscope having an eyepiece and a laser capture and microdissection subsystem configured to excise cells of interest from a sample and place them on a suitable medium is disclosed. The improvement takes the form of providing the machine with an augmented reality subsystem including a) a camera configured for capturing images of the field of view of the microscope; b) a machine learning model for identifying cells of potential interest within the images; c) an AR image generation unit and an optics module for overlaying an augmented reality image, e.g., enhancement onto the field of view as seen through the eyepiece in the form of an outline of potential cells of interest for LCM; and d) an operator activated input mechanism (e.g., switch) for invoking the laser capture and microdissection subsystem to excise the potential cells of interest in accordance with the augmented reality image from the sample and place the cells of interest in a suitable medium.

DETAILED DESCRIPTION

Figure 1:
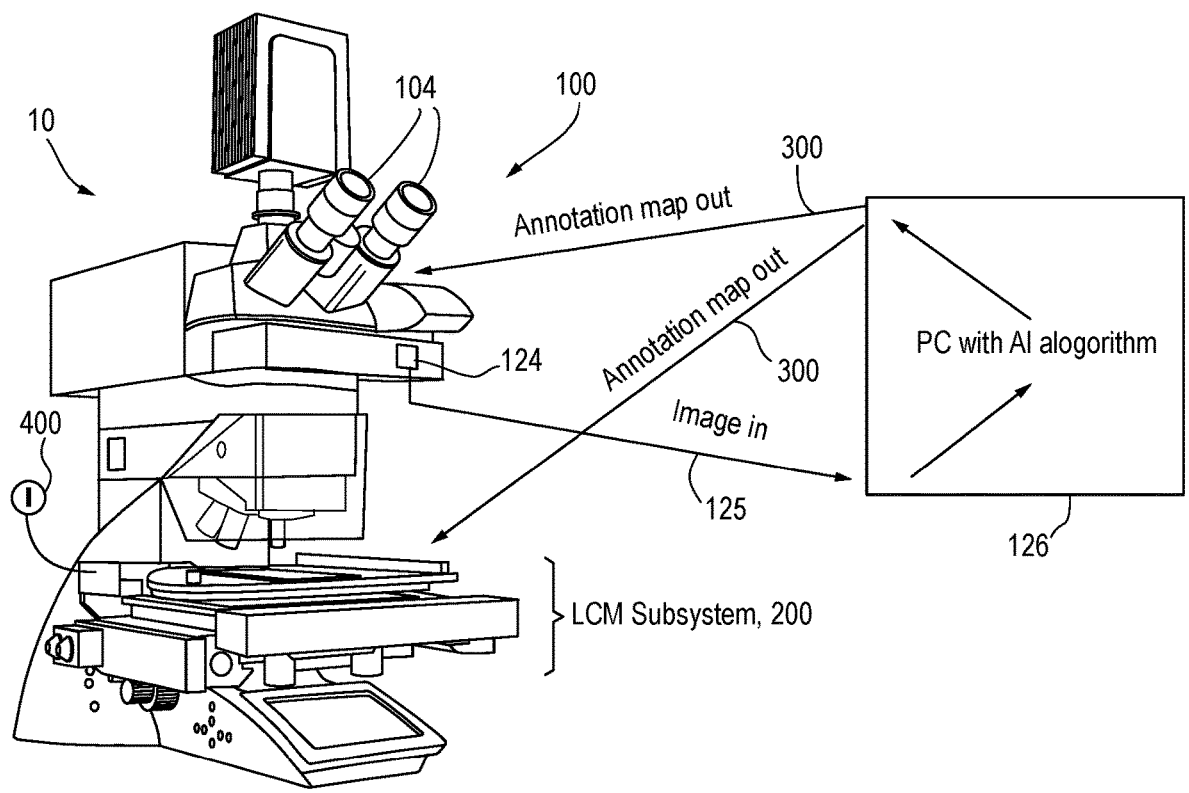
FIG. 1 is a schematic view of an LCM machine which is configured with an AR subsystem.

A system and method is described, which includes an augmented reality (AR) subsystem including one or more machine learning models, which operates to automatically overlay an augmented reality image, e.g., a border or outline, that identifies cells of potential interest, in the field of view of the specimen as seen through the eyepiece of LCM microscope. The operator does not have to manually identify the cells of interest for subsequent LCM, e.g., on a workstation monitor, as in the prior art. Rather, the areas of potential interest are identified automatically by the machine learning models in the AR subsystem and an augmented reality overlay image (e.g., border or outline) is provided in the field of view of the microscope so that the operator can see the tissue directly as well as the overlay identifying the cells or tissue of interest for LCM. The operator is provided with a switch, operator interface tool or other mechanism to select the identification of the cells, that is, indicate approval of the identification of the cells, while they view the specimen through the eyepiece. Activation of the switch or other mechanism invokes laser excising and capture of the cells of interest via a known and conventional LCM subsystem. Thus, this disclosure marries together two distinct technologies (1) a augmented reality microscope (and automatic identification regions which may be of interest for LCM), and (2) laser capture microdissection.

Two approaches to implementation of the system and method of this disclosure are contemplated:

1) integrate a LCM subsystem into an existing AR microscope system (e.g., as described in published PCT application WO 2018/231204). This requires providing the laser and sample capture subsystem, as provided in known, existing LCM machines, and integrating them with the AR microscope. The machine learning models of the AR microscope are developed to identify particular tissue or cell types of interest in LCM, for example the organ buds mentioned in Vincenzo Paduano et al., *Fully automated organ bud detection and segmentation for Laser Capture Microdissection applications*, 2011 IEEE International Conference on Imaging Systems and Techniques Penang, Malaysia (17-18 May 2011). The generation of an AR image and displaying it superimposed on the field of view seen through the eyepiece can be advantageously performed as described in WO 2018/231204. Furthermore, the data representing the outline or border in the augmented reality image is supplied to the LCM subsystem, thereby providing the X/Y coordinates within the sample for the cells of interest and therefore allow the laser to correctly execute the excising operation and capture of the cells of interest and place them on a suitable medium.

A variety LCM systems are known and provided by various manufacturers and described in the patent literature. See, for example, U.S. Pat. Nos. 9,804,144; 9,279,749; 9,664,599, the content of which are incorporated by reference.

2) add an AR subsystem to an existing LCM machine. This option requires the addition of the AR components, including a camera optically coupled to the LCM machine eyepiece capturing a magnified digital image of the field of view of the sample as seen through the eyepiece of the microscope (if not already present), and a computing unit including a machine learning model (artificial intelligence pattern recognizer) that receives the images from the camera and identifies areas or cells of interest in the sample from the data in the digital image. The LCM machine also is fitted with an optics module which incorporates a component, such as a semitransparent mirror or beam combiner/splitter, for overlaying an enhancement generated by the compute unit onto the field of view through the eyepiece. The optics module allows the operator to see the field of view of the microscope as they would in a conventional microscope of an LCM machine, and, on demand or automatically, see an enhancement (in this application, a boundary or outline of LCM tissue or cells of interest) as an overlay on the field of view which is projected into the field of view by an AR display generation unit and lens.

In either approach, as the operator moves the sample relative to the microscope optics in X and Y or changes magnification or focus, new images are captured by the camera and supplied to the machine learning pattern recognizer, and new region of interest boundaries are overlaid onto the field of view through the eyepiece. This display of new enhancements, superimposed on the field of view happens in substantial real time (i.e., within a few seconds or even fraction of a second) as the operator moves the slide relative to the microscope optics, changes focus, or changes magnification and continues to observe the specimen through the eyepiece. If the enhancement/boundary is of an area of interest, e.g., a cluster of cells, that the operator wants to be captured by LCM, they activate a switch or other suitable input mechanism (which can vary depending on the LCM configuration) which then causes laser excision of the cells of interest and subsequent capture of the cells in or on a suitable medium in the usual manner provided by the LCM machine.

Referring now to the drawings, FIG. 1 illustrates a LCM machine 10 which includes a augmented reality microscope subsystem 100 including binocular eyepieces 104 and a LCM subsystem 200 which performs laser capture and transport of excised cells from a sample in conventional manner. The specific techniques for laser capture, microdissection and transfer onto a suitable substrate or medium can vary widely and use any of the currently known LCM formats of the various manufacturers and described in the scientific and technical literature. Since these methods and the LCM subsystem (200) is known, a detailed description is omitted for the sake of brevity.

The LCM machine 10 includes a camera 124 which captures images of the field of view of the microscope as seen through the eyepieces. This image 125 (and in practice, typically a steady stream of images) is supplied to a compute unit 126, which may take the form of a general purpose computer which is equipped with one or more machine learning models. These models have been trained to identify cells of interest in the type of issue currently being examined, and at the current magnification of the microscope subsystem 100. A digital image 125 from the camera is fed to the appropriate model and the model identifies one or more clusters of cells of potential interest. The model may take the form of a deep convolutional neural network. The compute unit 126 generates an augmented reality enhancement to the field of view in the form of an image of a boundary or outline surrounding the cluster of cells of potential interest in the field of view. This enhancement is referred to as an "annotation map" 300 in FIG. 1. This annotation map is superimposed on the current field of view as seen through the eyepieces by projecting the annotation map into the field of view using an optics module as explained in detail in FIG. 2.

Further, this annotation map, or alternatively the data representing the outline, is provided to the LCM subsystem 200. The LCM subsystem uses the annotation map as input of the X/Y regions of the sample which are to be excised upon the receipt of a command or instruction from the operators. In particular, while the operator is viewing the specimen with the annotation map superimposed at the eyepiece of the microscope subsystem 100, the operator can decide to initiate LCM of the identified cluster of cells for LCM operation by activating an input mechanism, shown as a switch 400, or taking other operator interface action to initiate LCM action. For example, in FIG. 1, the LCM machine 10 includes an input mechanism in the form of a mouse 400 which is connected to the LCM subsystem and activating a click of the mouse the LCM is triggered. Alternatively, the input mechanism 400 could take the form of a foot switch, which when depressed by the operator triggers initiation of LCM. Alternatively, the input mechanism 400 could be integrated into the LCM machine 10 and be voice activated, e.g., by the operator speaking a designated command such as "cut" or "select."

Figure 2:
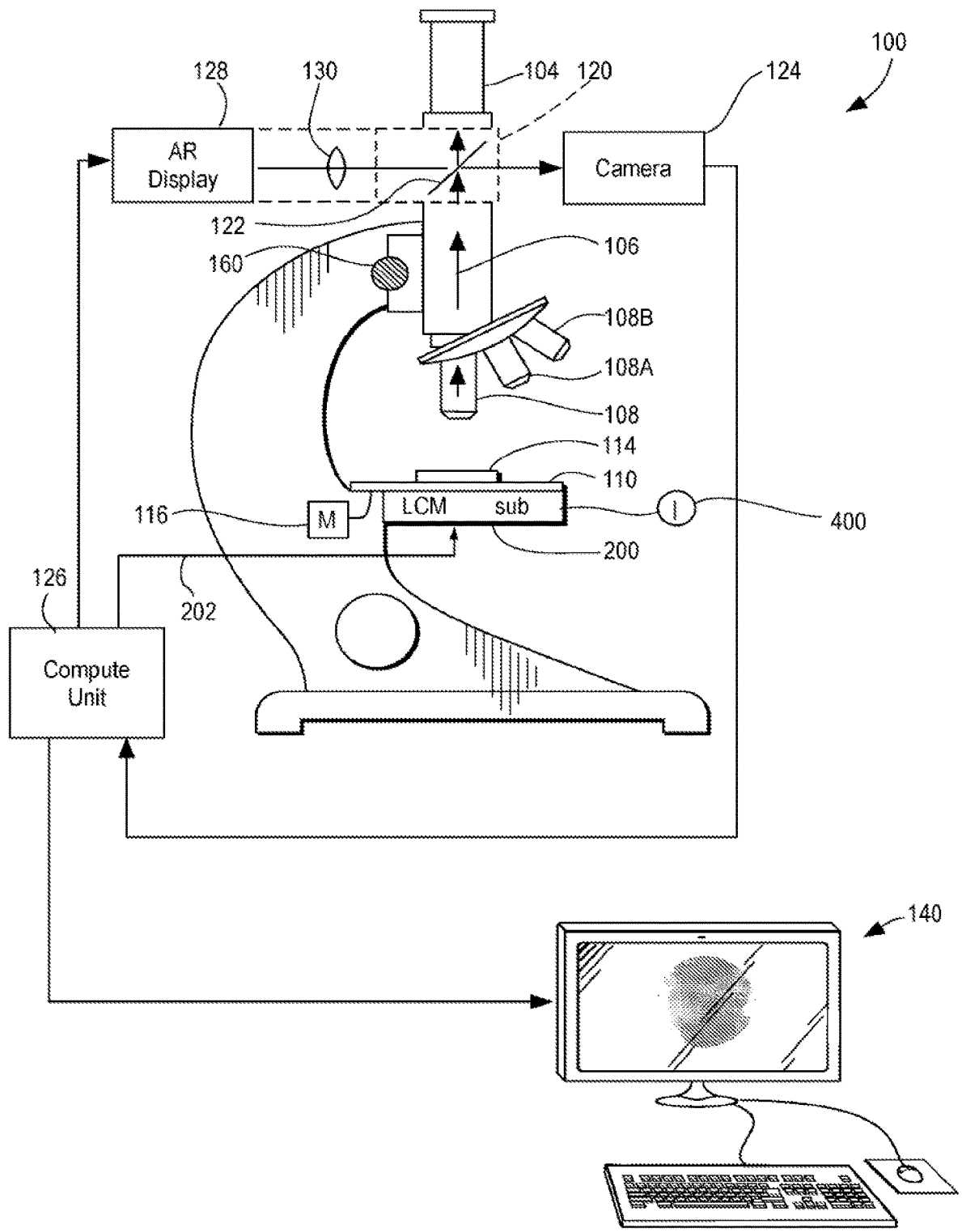
FIG. 2 is a schematic view of an augmented reality microscope which is configured with an LCM subsystem.

FIG. 2 is a schematic illustration of an augmented reality microscope 100 which is fitted with an LCM subsystem 200. The microscope 100 is described in detail in the patent literature, see WO 2018/231204 and in U.S. provisional application Ser. No. 62/656,557 filed Apr. 12, 2018, the content of which is incorporated by reference herein. FIG. 2 shows the augmented reality microscope 100 in conjunction with an optional connected pathologist workstation 140. The microscope includes an eyepiece 104 (optionally a second eyepiece in the case of a stereoscopic microscope). A stage 110 supports a slide 114 containing a biological sample. An illumination source (not shown) projects light through the sample. A microscope objective lens 108 directs an image of the sample as indicated by the arrow 106 to an optics module 120. Additional lenses 108A and 108B are provided in the microscope for providing different levels of magnification. A focus adjustment knob 160 allows the operator to change the depth of focus of the lens 108.

The optics module 120 incorporates a component, such as a semitransparent mirror 122 or beam combiner/splitter for overlaying an enhancement onto the field of view through the eyepiece. The optics module 120 allows the operator to see the field of view of the microscope as he would in a conventional microscope, and, on demand or automatically, see an enhancement (heat map, boundary or outline, annotations, "annotation map" of FIG. 1, etc.) as an overlay on the field of view which is projected into the field of view by an augmented reality (AR) display generation unit 128 and a lens 130. The image generated by the display unit 128 is combined with the microscope field of view by the semitransparent mirror 122. As an alternative to the semitransparent mirror, a liquid crystal display (LCD) could be placed in the optical path that uses a transmissive negative image to project the enhancement into the optical path.

The optics module 120 can take a variety of different forms, and various nomenclature is used in the art to describe such a module. For example, it is referred to as a "projection unit", "image injection module" or "optical see-through display technology." Literature describing such units include US patent application publication 2016/0183779 (see description of FIGS. 1, 11, 12, 13) and published PCT application WO 2016/130424A1 (see description of FIGS. 2, 3, 4A-4C); Watson et al., *Augmented microscopy: real-time overlay of bright-field and near-infrared fluorescence images*, Journal of Biomedical optics, vol. 20 (10) October 2015; Edwards et al., *Augmentation of Reality Using an Operating Microscope*, J. Image Guided Surgery. Vol. 1 no. 3 (1995); Edwards et al., *Stereo augmented reality in the surgical microscope*, Medicine Meets Virtual Reality (1997) J. D. Westward et al (eds.) IOS Press, p. 102.

The semi-transparent mirror 122 directs the field of view of the microscope to both the eyepiece 104 and also to a digital camera 124. A lens for the camera is not shown but is conventional. The camera may take the form of a high resolution (e.g., 16 megapixel) video camera operating at say 10 or 30 frames per second. The digital camera captures magnified images of the sample as seen through the eyepiece of the microscope. Digital images captured by the camera are supplied to a compute unit 126. Alternatively, the camera may take the form of an ultra-high resolution digital camera such as APS-H-size (approx. 29.2×20.2 mm) 250 megapixel CMOS sensor developed by Canon and announced in September 2015.

Briefly, the compute unit 126 includes a machine learning pattern recognizer which receives the images from the camera. The machine learning pattern recognizer may take the form of a deep convolutional neural network which is trained on a large set of microscope slide images of the same type as the biological specimen under examination. Additionally, the pattern recognizer will preferably take the form of an ensemble of pattern recognizers, each trained on a set of slides at a different level of magnification, e.g., 5×, 10×, 20×, 40×. The pattern recognizer is trained to identify regions of interest in an image (the exact type which will vary depending on the specific application of LCM under consideration) in biological samples of the type currently placed on the stage. The pattern recognizer recognizes regions of interest on the image captured by the camera 124. The compute unit 126 generates data representing an enhancement to the view of the sample as seen by the operator, in this example in the form of a closed curve or boundary, which is generated and projected by the AR display unit 128 and combined with the eyepiece field of view by the semitransparent mirror 122.

Other machine learning approaches can be used to identify the regions of interest. See Vincenzo Paduano et al., *Fully automated organ bud detection and segmentation for Laser Capture Microdissection applications*, 2011 IEEE International Conference on Imaging Systems and Techniques Penang, Malaysia (17-18 May 2011); Brasko et al., *Intelligent image-based in situ single-cell isolation*, Nature Communications Vol. 9 article no. 226 (January 2018); Bing et al, U.S. Patent Application Publication no. 2018/0114317.

The essentially continuous capture of images by the camera 124, rapid performance of inference on the images by the pattern recognizer, and generation and projection of enhancements as overlays onto the field of view, enables the microscope of FIG. 2 to continue to provide enhancements to the field of view and assist the pathologist in selecting cells of interest in the specimen for LCM in substantial real time as the operator navigates around the slide (e.g., by use of a motor 116 driving the stage), by changing magnification by switching to a different objective lens 108A or 108B, or by changing depth of focus by operating the focus knob 160.

By "substantial real time," we mean that an enhancement or overlay is projected onto the field of view within 10 seconds of changing magnification, changing depth of focus, or navigating and then stopping at a new location on the slide. In practice, as explained below, with the optional use of inference accelerators, we expect that in most cases the new overlay can be generated and projected onto the field of view within a matter of a second or two or even a fraction of a second of a change in focus, change in magnification, or change in slide position.

The above description is also applicable to the system of FIG. 1 and the LCM machine of FIG. 1 is outfitted with the augmented reality subsystem of the microscope of FIG. 2, including the camera 124 (if not already present), the compute unit 126, and the optics module 120.

Note further that in FIG. 2 the enhancement or annotation map generated in the compute unit 126 (or data representing the outline of the annotation map) is also provided to the LCM subsystem 200 so as to enable the LCM subsystem to perform laser excision of the cells of interest at the correct X/Y location in the specimen and capture of the cells in a suitable medium in accordance with the enhancement on the field of view as seen by the operator.

When the operator uses the instrument of FIG. 2 and wishes to initiate an LCM operation, they activate the switch 400 of FIG. 2 and the LCM laser capture and microdissection operations commence.

The operator then continues to navigate around the slide, change focus, change magnification, etc. as they see fit and meanwhile the compute unit continues to generate new boundaries of cells of potential interest which are displayed in the field of view of the microscope. The operator continues to activate the LCM subsystem as desired to capture additional cells of interest by activating the switch 400. When the operator is done with a particular specimen (microscope slide) they select a new one, it is placed on the stage 110 and the process continues as explained above.

Figure 3A:
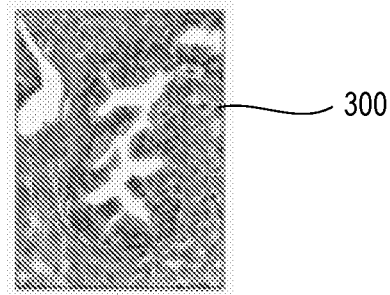
FIG. 3A is an illustration of the view through the eyepiece of an LCM machine which does not have the AR aspect of this disclosure.

FIG. 3A is an illustration of the view through the eyepiece of an LCM machine which does not have the AR aspect of this disclosure. The operator views a sample 300, and a cluster of cells in roughly the center of FIG. 3, but they still have to manually draw the boundary over cluster of cells of interest, e.g., with the aid of drawing tools and an external monitor.

Figure 3B:
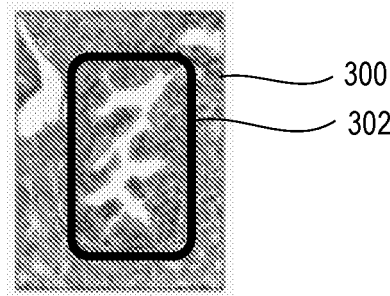
FIG. 3B is an illustration of the view through the eyepiece of an LCM machine which does have the AR aspect of this disclosure, e.g., the instrument of either FIG. 1 or FIG. 2, showing the cells of potential interest for LCM surrounded by a border; if the operator is satisfied that the cells of interest should be captured they activate a switch or other suitable control device to trigger operation of the LCM subsystem.

FIG. 3B is an illustration of the view through the eyepiece of an LCM machine which does have the AR aspect of this disclosure, e.g., the instrument of either FIG. 1 or FIG. 2, showing the cells of potential interest for LCM surrounded by a border 302; if the operator is satisfied that the cells of interest should be captured they activate the switch 400 or other suitable control device to trigger operation of the LCM subsystem of FIG. 1 or FIG. 2.

Figure 3C:
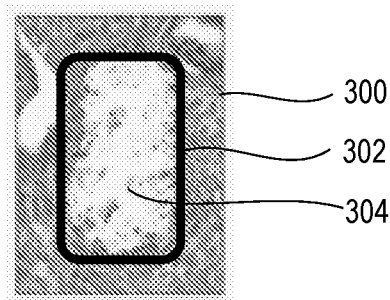
FIG. 3C is the view of the specimen after the microdissection operation.

FIG. 3C is the view of the specimen after the microdissection operation. The cells within the border 300 are now removed from the view through the microscope eyepiece as indicated by the vacant area 304, indicating that the LCM operation to remove the cells from the sample slide and place them in a suitable medium has occurred.

The details of the compute unit 126 of FIGS. 1 and 2 are described in the previously cited patent literature, therefore a detailed description will be omitted. In a typical implementation it includes a deep convolutional neural network pattern recognizer in the form of a memory storing processing instructions and parameters for the neural network and a central processing unit or performance of inference on a captured image. The module may also include a graphics card generating overlay digital data (e.g. annotations, outlines, etc.) based on the inference results from the pattern recognizer. A memory includes processing instructions for selecting the appropriate machine learning model based on the current magnification level. The compute unit may also include an inference accelerator to speed up the performance of inference on captured images. The compute unit further includes various interfaces to other components of the system including an interface, not shown, to receive the digital images from the camera, such as a USB port, an interface (e.g., network cable port or HDMI port) to send digital display data to the AR display unit 128, an interface (e.g., network cable port) 202 to the workstation 140 or to the LCM subsystem 200 and an interface (e.g., SC card reader) enabling the compute unit to receive and download portable media containing additional pattern recognizers to expand the capability of the system to perform pattern recognition and overlay generation for different pathology applications. In practice, additional hard disk drives, processors, or other components may be present in the compute unit, the details of which are not particularly important.

In another possible configuration, the compute unit 126 could take the form of a general purpose computer (e.g., PC) augmented with the pattern recognizer(s) and accelerator, and graphics processing modules. The personal computer has an interface to the camera (e.g., a USB port receiving the digital image data from the camera), an interface to the AR projection unit 126, such as an HDMI port, and a network interface to enable downloading of additional pattern recognizers and/or communicate with a remote workstation as shown in FIG. 2.

In use, assuming multiple different pattern recognizers are loaded into the compute unit, an automatic specimen type detector or manual selector switches between the specimen dependent pattern recognition models (e.g. prostate cancer vs breast cancer vs organ bud detection), and based on that the proper machine learning pattern recognizer or model is chosen. Movement of the slide to a new location (e.g., by use of a motor 116 driving the stage) or switching to another microscope objective 108 (i.e. magnification) triggers an update of the enhancement, as explained previously. Optionally, if only the magnification is changed, an ensemble of different models operating at different magnification levels performs inference on the specimen and inference results could be combined on the same position of the slide. Further details on how this operation could be performed are described in the pending PCT application entitled "Method and System for Assisting Pathologist Identification of Tumor Cells in Magnified Tissue Images", serial no. PCT/US17/019051, filed Feb. 23, 2017, published as WO 2018/156133, the content of which is incorporated by reference herein. Another option is that the compute unit could know the current magnification from the microscope by means of simple electronic communication from the microscope to the compute unit. The microscope monitors which lens is placed by the operator into the optical path and communicates the selection to the compute unit.

Deep convolutional neural network pattern recognizers, of the type used in the compute unit of FIGS. 1 and 2, are widely known in the art of pattern recognition and machine vision, and therefore a detailed description thereof is omitted for the sake of brevity. The Google Inception-v3 deep convolutional neural network architecture, upon which the present pattern recognizers are based, is described in the scientific literature. See the following references, the content of which is incorporated by reference herein: C. Szegedy et al., *Going Deeper with Convolutions*, arXiv:1409.4842 [cs.CV] (September 2014); C. Szegedy et al., *Rethinking the Inception Architecture for Computer Vision*, arXiv: 1512.00567 [cs.CV] (December 2015); see also U.S. patent application of C. Szegedy et al., "Processing Images Using Deep Neural Networks", Ser. No. 14/839,452 filed Aug. 28, 2015. A fourth generation, known as Inception-v4 is considered an alternative architecture for the pattern recognizers 306. See C. Szegedy et al., *Inception-v4, Inception-ResNet*

*and the Impact of Residual Connections on Learning*, arXiv: 1602.0761 [cs.CV] (February 2016). See also U.S. patent application of C. Vanhoucke, "Image Classification Neural Networks", Ser. No. 15/395,530 filed Dec. 30, 2016. The description of the convolutional neural networks in these papers and patent applications is incorporated by reference herein.

Additional literature describing deep neural network pattern recognizers include the following G. Litjens, et al., *Deep learning as a tool for increasing accuracy and efficiency of histopathological diagnosis*, www.nature.com/scientificreports 6:26286 (May 2016): D. Wang et al., Deep Learning for Identifying Metastatic Breast Cancer, arXiv: 1606.05718v1 (June 2016); A. Madabhushi et al., *Image analysis and machine learning in digital pathology: Challenges and opportunities*, Medical Image Analysis 33 p 170-175 (2016); A. Schuamberg, et al., *H&E-stained Whole Slide Deep Learning Predicts SPOP Mutation State in Prostate Cancer*, bioRxiv preprint.

As noted previously, the LCM transfers the cells of interest onto a suitable medium. The term "suitable medium" in intended to refer broadly to known substrates, containers and/or and media which are specifically adapted for use in LCM, such as for example the transfer films described in U.S. Pat. Nos. 9,279,749 and 9,103,757. As explained in the '749 patent, some embodiments of laser microdissection employ a polymer transfer film that is placed on top of the tissue sample. The transfer film may or may not contact the tissue sample. This transfer film is typically a thermoplastic manufactured containing organic dyes that are chosen to selectively absorb in the near infrared region of the spectrum overlapping the emission region of common AlGaAs infrared laser diodes. When the film is exposed to the focused laser beam the exposed region is heated by the laser and melts, adhering to the tissue in the region that was exposed. The film is then lifted from the tissue and the selected portion of the tissue is removed with the film. Thermoplastic transfer films such as a 100 micron thick ethyl vinyl acetate (EVA) film available from Electroseal Corporation of Pompton Lakes, N.J. (type E540) have been used in LCM applications. The film is chosen due to its low melting point of about 90° C. As another example, see the description of the capture membranes in U.S. Pat. No. 8,664,002. As another example, the suitable medium may be a surface or solution present in a receiving container, as described in U.S. Pat. No. 9,664,599, and catching devices, micropipettes, and other apparatus may be used in transferring the cells and placing them in a receiving container or on a film or substrate. Another example of a suitable medium is a reaction vial, described in U.S. Pat. Nos. 7,915,016 and 5,998,129.

While presently preferred embodiments have been described in detail, it will be appreciated by those skilled in the art that variation from the specifics of such embodiments can be made without departure from the scope of this disclosure. All questions concerning scope are to be determined by reference to the appended claims.

We claim:

1. An augmented reality laser capture microdissection machine for capturing cells of interest from a sample, comprising, in combination;
   a) a microscope having an eyepiece and a camera configured to capture images of a field of view of the microscope as seen through the eyepiece;
   b) an augmented reality subsystem configured to receive the images from the camera, the subsystem including a machine learning model stored on a non-transitory machine readable medium identifying cells of potential interest in the images and a optics module projecting into a view of the microscope as seen through the eyepiece an outline of cells of potential interest identified by the machine learning model;
   c) a laser capture and microdissection subsystem configured for excising the cells of interest from the sample with one or more lasers and placing such cells of interest on a suitable medium; and
   d) an operator-activated input mechanism configured to provide input to the laser capture and microdissection subsystem whereby operator activation of the input mechanism while viewing the specimen and the outline of cells identified by the machine leaning model at the eyepiece invokes the laser capture and microdissection subsystem so as to excise the cells of interest from the sample within the outline and place them on the medium.

2. The machine of claim 1, wherein the operator-activated mechanism is configured so as to permit the operator to activate the mechanism while viewing the specimen though the eyepiece.

3. The machine of claim 2, wherein the mechanism is activated by a voice command.

4. The machine of claim 2, wherein the mechanism is activated by a foot switch.

5. The machine of claim 2, wherein the mechanism is activated by a mouse or keyboard stroke.

6. The machine of claim 1, wherein the machine learning model comprises a deep convolutional neural network.

7. The machine of claim 1, wherein the augmented reality subsystem includes a multitude of machine learning models for different tissue types and magnification levels.

8. A method of capturing cells of interest from a sample using a microscope having an eyepiece, comprising the steps of:
   a) projecting an augmented reality image into a field of view of the microscope as seen through the eyepiece, the augmented reality image identifying cells of potential interest for laser capture microdissection; and
   b) invoking a laser capture and microdissection subsystem coupled to the microscope so as to excise the cells of potential interest, as presented in the augmented reality image, from the sample in response to an operator instruction.

9. The method of claim 8, wherein the augmented reality image comprises a border surrounding cells of potential interest.

10. The method of claim 8, wherein the operator instruction comprises a voice command.

11. The method of claim 8, wherein the operator instruction comprises activation of a foot switch.

12. The method of claim 8, wherein the operator instructions comprises a mouse click or keyboard stroke.

13. The method of claim 8, wherein the method comprises the step of repeating steps a) and b) as an operator of the microscope changes magnification or performs zoom operations while viewing the sample with the microscope.

14. The method of claim 8, wherein step b) wherein the operator instruction is received while the operator of the microscope is viewing the specimen through the eyepiece of the microscope.

15. In a machine including a microscope having an eyepiece and a laser capture and microdissection subsystem configured to excise cells of interest from a sample and place them on a suitable medium, the improvement comprising:

providing said machine with an augmented reality subsystem comprising:
a) a camera for capturing images of a field of view of the microscope;
b) a machine learning model for identifying cells of potential interest within the images;
c) an augmented reality (AR) image generation unit and an optics module for overlaying an enhancement onto the field of view as seen through the eyepiece in a form of an outline of potential cells of interest for laser capture microdissection (LCM); and
d) an operator activated input mechanism for invoking the laser capture and microdissection subsystem to excise the potential cells of interest in accordance with the enhancement from the sample and place the cells of interest in a suitable medium.

* * * * *